US00PP34101P2

(12) United States Plant Patent
Hansen

(10) Patent No.: US PP34,101 P2
(45) Date of Patent: Apr. 5, 2022

(54) ***PHLOX* PLANT NAMED 'OPENING ACT ROMANCE'**

(50) Latin Name: ***Phlox* hybrid**
Varietal Denomination: Opening Act Romance

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,858

(22) Filed: Nov. 29, 2021

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

*Primary Examiner* — Kent L Bell

(57) ABSTRACT

A new and unique hybrid cultivar of *Phlox* plant named *Phlox* 'Opening Act Romance' multi-stemmed, medium height, upright, slowly-spreading habit with clean, medium-green, glossy, lanceolate leaves with exceptional powdery mildew resistance. Foliage is thick and leathery on stiff stems. Flowers are rich lavender-pink flowers with a white halo in the center, produced on branched peduncles and nearly cover the top of the plant beginning early summer, about two weeks prior to typical *Phlox paniculata* cultivars, known to the Inventor continuing for about five weeks and reblooming through late summer. 'Opening Act Romance' is especially suitable as a potted plant, for the garden, for attracting hummingbirds and butterflies, and for cut flower arrangements.

1 Drawing Sheet

Botanical classification: *Phlox* hybrid.
Variety denomination: 'Opening Act Romance'.

STATEMENT REGARDING PRIOR DISCLOSURES UNDER 37 CFR 1.77(b)(6)

The first non-enabling brief description and photograph occurred on Dec. 1, 2020 on a website owned and operated by Walters Gardens, Inc. Subsequently, Walters Gardens, Inc. published their non-enabling "Walters Gardens 21-22 Catalog" on May 21, 2021 with a brief description and photograph. The first disclosure, in the form of a sale, was made by Walters Gardens, Inc. on Mar. 23, 2021 to Midwest Groundcover Nursery followed by sales to numerous other nurseries. Walters Gardens, Inc. obtained the new plant and all information relating thereto, from the inventor. No plants of *Phlox* 'Opening Act Romance' have been sold, in this country or anywhere in the world, under this or any name, nor has any disclosure of the new plant been made more than one year prior the filing date of this application, and such sale or disclosure within one year was either derived directly or indirectly from the inventor.

BACKGROUND OF THE INVENTION

The present invention relates to a new and distinct hybrid cultivar of *Phlox* plant, known as *Phlox* 'Opening Act Romance' and will be referred to hereafter by its cultivar name or the "new plant". The new plant was the result of self-pollination of the proprietary, unreleased hybrid named only by the breeder code number 14-17 (not patented). The pollination was performed by the inventor on Aug. 7, 2014, in the greenhouses at a wholesale perennial nursery in Zeeland, Mich. During the trial process the new plant was identified by the breeder code 14-633-3. 'Opening Act Romance' has been asexually propagated by tip and basal stem cuttings in the greenhouses at the same nursery in Zeeland, Mich. since 2016, as well as by shoot tip tissue culture. The unique characteristics of the new plant have been found to be reproducible and stable in successive generations of asexually propagated plants and the resultant plants have been found to be identical to the original selection.

BRIEF SUMMARY OF THE PLANT

*Phlox* 'Opening Act Romance' is unique from its parents and all other tall garden *Phlox* or other hybrid *Phlox* known to the inventor. The closest comparison cultivars known to the inventor are *Phlox* 'Opening Act Ultrapink' U.S. Plant Pat. No. 32,093, 'Cloudburst' U.S. Plant Pat. No. 30,289, 'Kung Fuchsia' U.S. Plant Pat. No. 31,308, 'Fashionably Early Flamingo' U.S. Plant Pat. No. 29,911 and 'Fashionably Early Princess' U.S. Plant Pat. No. 28,680.

The new plant differs from the parent in that the parent is taller in habit with wider foliage and has lighter colored flowers. 'Amethyst Pearl' U.S. Plant Pat. No. 28,487 has broader leaves, lighter amethyst-pink flowers without a white eye and the flowers are more concentrated on the upper plain. 'Lil' Cahaba' (not patented) has narrower foliage with pinky-mauve-colored flowers without a white eye, and the petals do not overlap as much.

'Opening Act Ultrapink' has a slightly taller habit with flowers that are a brighter, fluorescent rose-pink without a white eye. 'Cloudburst' is taller in habit and has more lavender purple flowers with smaller bright pink eyes. 'Kung Fuchsia' is slightly shorter in habit and has bright fuchsia-pink flower faces with light pink eye zones markings and lacks the white eye. 'Fashionably Early Flamingo' has taller and broader habit with larger foliage and larger inflorescence and the flowers are lavender-pink. 'Fashionably Early Princess' has flowers of light fuchsia-pink with a darker pink eye on slightly taller plants.

'Opening Act Romance' differs from all other *Phlox* known to the inventor in the following repeatedly observed traits in combination:

1. Plants of medium height, upright habit, slowly spreading by short rhizomes, producing clean, leathery, glossy, medium-green, narrowly lanceolate leaves;
2. Showing exceptional powdery mildew resistance;
3. Multiple branched, stems produce branched mounds of flowers;
4. Flower on strong stiff stems of about 45.0 cm tall producing rich lavender-pink flowers with a white halo in the center;
5. Flowers cover nearly the entire top of the plant;
6. Flowering beginning in early-summer about two weeks prior to typical *Phlox paniculata* cultivars known to the Inventor and re-blooming through late-summer.

BRIEF DESCRIPTION OF THE DRAWINGS

The photographs of the new plant demonstrate the unique traits of 'Opening Act Romance' and the overall appearance of three-year-old plants grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
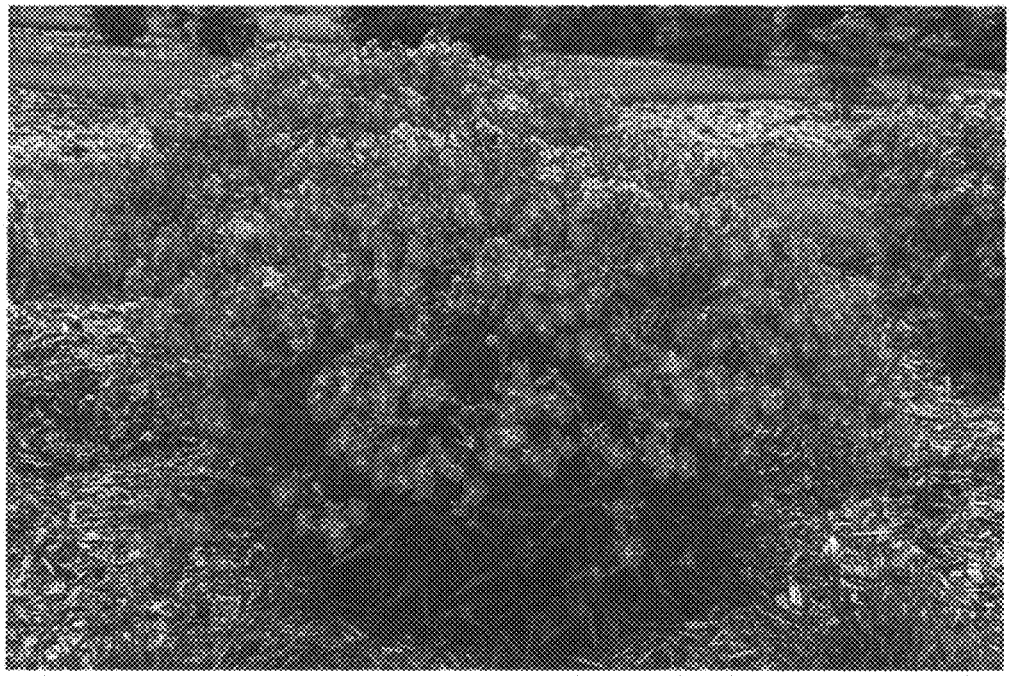
FIG. 1 shows the new plant habit in peak flower in the landscape.
Figure 2:
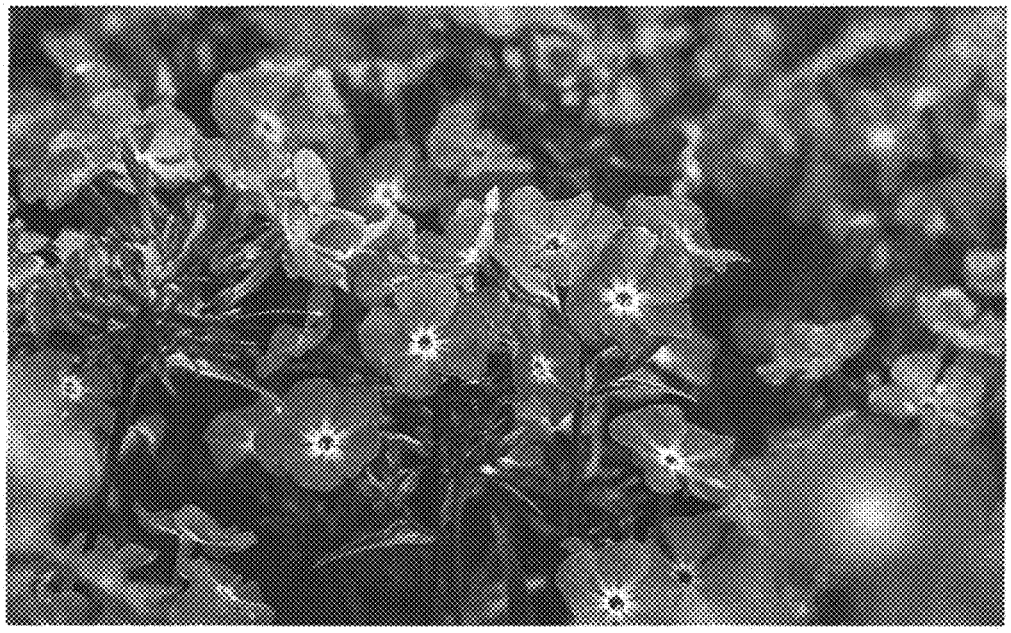
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Opening Act Romance' has not been observed under all possible environments. The phenotype may vary slightly with different growing environments such as temperature, light, fertility, soil pH, moisture and maturity levels, but without any change in the genotype. The following observations and size descriptions are based on two-year-old plants in the partially shaded greenhouse and three-year-old plants in the trial gardens of a wholesale perennial nursery in Zeeland, Michigan with supplemental fertilizer and water as needed.

Botanical classification: *Phlox* hybrid;

Parentage: The parent is the proprietary hybrid 14-17, which consists of a cross between 'Amethyst Pearl' U.S. Plant Pat. No. 28,487 times 'Lil' Cahaba' (not patented);

Plant habit: Hardy herbaceous perennial, densely upright, producing about 30 rigid mostly upright stems; flowering about 56.0 cm tall and about 90.0 cm wide; flowering begins early summer in Michigan and continuing for about 5 weeks and repeating into late summer;

Propagation: Stem cuttings; rooting in about 14 days;

Time to produce finished crop in 3.8-liter pots: About 8 to 10 weeks; moderate rate of growth;

Root: Primary roots to about 1.0 mm thick; secondary fibrous and freely branching; color creamy white to tan depending on soil type;

Leaves: Simple; opposite; sessile; narrowly lanceolate; narrowly acute apex; rounded to truncate base; entire margin with micro-ciliolate in basal margin portion; coriaceous;

Leaf size: To about 13.5 cm long by about 18.0 mm wide, average about 11.4 cm long by about 16.0 mm wide; becoming shorter and broader distally;

Leaf surfaces: Glabrous and lustrous adaxial and glabrous and matte abaxial;

Leaf color expanding: Adaxial between RHS 143A and RHS 146B, abaxial nearest RHS 138A;

Leaf color at flowering: Adaxial nearest RHS 137A, abaxial between RHS 138A and RHS 146A;

Foliage fragrance: None detected;

Veins: Pinnate; glabrous and slightly lustrous both adaxial and abaxial; midrib about 1.5 mm wide at base, slightly sunken adaxial and costate abaxial;

Vein color: Adaxial nearest RHS 137A with midrib nearest RHS 145A, abaxial between RHS 146D and RHS 138A with midrib between RHS 145A and RHS 146D;

Petiole: Leaves sessile;

Stems: About 60 per three-year-old plant; terete; stiff; wiry; strong; mostly upright; glabrous; to about 43.0 cm, average about 40.0 cm long and 4.0 mm diameter at base;

Stem color: Nearest RHS 146D with a moderate blush in the distal region of nearest RHS 187B;

Nodes: About ten per stem below initial flowers; average internode length about 4.3 cm;

Node color: Nearest RHS 145A;

Inflorescence: A loosely branched compound corymb of about 45 flowers; initial flowering portion about 13.0 cm long and 13.0 cm across;

Flowers: Perfect; salverform with flat face and long fused tube; actinomophic; typically with five petals; about 30.0 mm long total, with tube about 29.0 mm long and 2.5 mm diameter; face about 27.0 mm across; attitude upright to slightly outward; self-cleaning;

Flower longevity: Individually about 5 days on plant or as cut flower;

Flower fragrance: Lightly sweet;

Buds one to two days prior to opening: Narrowly oblanceolate, to nearly clavate; acute apex with petals implicate about each other; base fused; total bud about 28.0 mm long, tube about 18.0 mm long and 2.5 mm diameter in tube, bulb 10.0 mm long and swollen to 7.0 mm diameter toward apex of convolute petals;

Bud color: Petals nearest RHS N82D in bulb and between RHS 77A and RHS N77B in corolla tube and nearest RHS 145C where bulb and tube join;

Petals: Five; margin entire; apex rounded; base fused into corolla tube; abaxial and adaxial limb glabrous, abaxial tube surface glabrous, adaxial tube glabrous except pubescent with hairs nearest RHS 4D in the 4.0 mm region beginning about 4.0 mm from base; limbs imbricate to about 10 percent over the next petal;

Petal size: Limb to about 11.0 mm wide and about 13.0 mm long, corolla tube to about 29.0 mm long and 3.0 mm diameter at face;

Petal color: (Young) adaxial limb nearest RHS N80B with basal 2.0 mm making up eye nearest RHS 155C; abaxial limb nearest RHS 76B; adaxial corolla tube basal 3.0 mm nearest RHS 155C, distally between RHS 77A and RHS N81A; abaxial corolla tube basal 3.0 mm nearest RHS 145D, distally between RHS N81B and RHS N81C;

Petal color: (Mature) adaxial limb nearest RHS N80A with 2 mm in center making up eye nearest RHS NN155D, adaxial corolla tube basal 3.0 mm nearest RHS 155D distally between RHS 77A and RHS N81A; abaxial limb nearest 76B, abaxial corolla tube basal 3.0 mm nearest RHS 145D, distally between RHS N81B and RHS N81C;

Androecium: Five;

*Filaments.*—Typically five; adnate to adaxial corolla tube except free in terminal 0.5 mm; varying lengths between 22.0 mm and 27.0 mm, less than 0.3 mm in diameter; color nearest RHS NN155D distally and nearest RHS 145D in the basal 4.0 mm.

*Anther.*—Five; oblong elliptic; dorsifixed; longitudinal; about 3.0 mm long by 1.2 mm wide; color nearest RHS 13A.

*Pollen.*—Abundant; color nearest RHS 15A.

Gynoecium: One pistil per flower; to about 24.0 mm long;

*Style.*—Cylindrical; straight; about 21.0 mm long and about 0.2 mm diameter; persistent after flower abscission; color nearest RHS 145D.

*Stigma.*—Trifid in the distal 1.0 mm, about 0.3 mm in diameter; color nearest RHS 11A.

*Ovary.*—Superior; conical; acute apex, base truncate; about 2.0 mm long and 1.0 mm diameter; color nearest RHS 144A.

Calyx: Tubular; connate to corolla tube; to about 9.0 mm long and 3.0 mm cross at apex;

Sepals: Five; lanceolate; narrowly acute apex, margin entire; basal 4.0 mm fused; adaxial and abaxial surface matte; persistent; individually about 9.0 mm long and 1.5 mm wide just above fusion;

Sepal color: Adaxial distally nearest RHS 141B with margin and fusion line transparent to translucent and basally nearest RHS 146D with light to moderate blush of anthocyanin nearest RHS 187B; abaxial distally nearest RHS 137B with margins and fusions transparent to translucent and basally nearest RHS 146D with light to moderate blush of anthocyanin nearest RHS 187B;

Peduncle: Glabrous, stiff, strong, moderately lustrous and micro-puberulent, upright, cylindrical; to about 24.0 cm long and 2.0 mm diameter at base of flower branches and about 4.0 mm diameter near soil; branches to about 22.0 mm long and 2.0 mm diameter at base;

Peduncle color: Nearest blend of RHS 145A and RHS 146D;

Bracts: Subtending upper branches and flowers; lanceolate; ciliolate margin; narrowly acute apex; sessile truncate base; to about 4.0 cm long and 1.3 cm across at base; same colors as leaves;

Pedicel: Cylindrical; micro-puberulent; to about 2.0 mm long and 1.0 mm diameter;

Pedicel color: Nearest RHS 146C without anthocyanin blush;

Fruit and seeds have not yet been observed.

Hardiness and culture: The new plant grows best with plenty of moisture and adequate drainage; hardy to at least from USDA zone 4 through 8.

Disease and pest resistance: *Phlox* 'Opening Act Romance' demonstrated the excellent powdery mildew resistance caused by *Erysiphe cichoracearum* in the presence and under conditions of intense pressure that would normally show symptoms.

I claim:

1. A new and distinct cultivar of hybrid *Phlox* plant named *Phlox* 'Opening Act Romance', as herein described and illustrated.

* * * * *